United States Patent [19]
Guttman

[11] Patent Number: 5,296,116
[45] Date of Patent: Mar. 22, 1994

[54] CAPILLARY ELECTROPHORESIS USING TIME-VARYING FIELD STRENGTH

[75] Inventor: Andras Guttman, Corona, Calif.

[73] Assignee: Beckman Instruments, Inc., Fullerton, Calif.

[21] Appl. No.: 900,223

[22] Filed: Jun. 17, 1992

[51] Int. Cl.$^5$ .................... G01N 27/26; G01N 27/447
[52] U.S. Cl. .............................. 204/180.1; 204/182.8; 204/299 R
[58] Field of Search .............. 204/182.8, 180.1, 299 R

[56] References Cited

U.S. PATENT DOCUMENTS

| | | | |
|---|---|---|---|
| 4,909,919 | 3/1990 | Morris et al. | 204/299 R |
| 4,959,133 | 9/1990 | Adcock | 204/299 R X |
| 5,015,350 | 5/1991 | Wiktorowicz | 204/180.1 |
| 5,122,248 | 6/1992 | Karger et al. | 204/182.8 |

OTHER PUBLICATIONS

Walton L. Fangman "Separation of very large DNA molecules by gel electrophoresis" Nucleic Acids Research, vol. 5. No. 3 (1978) 653–665.
David N. Heiger, Aharon S. Cohen, and Barry L. Karger "Separation of DNA restriction fragments by high performance capillary electrophoresis with low and zero crosslinked polyacrylamide using continuous and pulsed electric fields" Journal of Chromatography, 516 (1990) 33–48.
Cohen, A. S.; Proc. Natl. Acad. Sci. USA, 1988, 85, 9660–9663.
Paulus, A.; Electrophoresis, 1990, 11, 702–708.
Yin, H. F.; High Res. Chrom., 1990, 13, 624–627.
Guttman, A.; Anal. Chem., 1990, 62, 2038–2042.
Schwartz, H. E.; J. Chromatogr., 1991, 559, 267–283.
Heiger, D. N.; J. Chromatogr., 1990, 516, 33–48.
Guttman, A.; J. Chromatogr., 1991, 559, 285–294.
Guttman, A.; J. Chromatogr., 1991, 593, 297–303.
Dennison, C.; Anal. Biochem., 1982, 120, 12–18.
Biggin, M.D.; Proc. Natl. Acad. Sci. USA, 1983, 80, 3963–3965.
Ansorge, W.; J. Biochem. Biphys. Methods, 1984, 10, 237–243.
Cantor, C. R.; Ann. Rev. Biophys. Biophys. Chem., 1988, 287–304.
Fangman, W. L.; Nucl. Acid Res., 1978, 5, 653–665.
Demana, T.; Anal. Chem., 1991, 63, 2795–2797.
Flint, D. H., Biochemistry, 1972, 11, 4858–4864.
Smizek, D. L.; Science, 1990, 248, 1221–1223.
De Gennes, P. G.; Scaling Concepts in Polymer Physics, Cornell University Press, Ithaca, N.Y., Ch. 3, 1979.
Lumpkin, O. J.; Biopolymers, 1985, 24, 1573–1593.
Slater, G. W.; Biopolymers, 1986, 25, 431–454.
Guttman, A.; Anal. Chem., 1991, 61, 2038–2042.
Karger, B. L.; J. Chromatogr., 1989, 492, 585–614.

Primary Examiner—John Niebling
Assistant Examiner—John S. Starsiak, Jr.
Attorney, Agent, or Firm—William H. May; P. R. Harder; Wen Liu

[57] ABSTRACT

The present invention is directed to a technique that provides enhanced separation resolution in electrophoresis. This technique involves the use of a time-varying field strength, which may be progressively increasing or decreasing, constant or otherwise, as a function of time. The shape of the field strength with respect to time may be continuous or stepwise over time, monotonic or otherwise.

Because the mobility of different size species is a function of the applied electric field, the use of a nonuniform (time varying) electric field increases the resolving power of electrophoresis. This technique has been found to provide enhanced resolution of double-stranded DNA molecules in capillary polyacrylamide gel electrophoresis. It has been found that enhanced separation of DNA restriction fragments of 1 to more than 1000 base pairs in size has been achieved employing the technique of the present invention.

9 Claims, 6 Drawing Sheets

| PEAK # | BASE PAIRS | 100 V/cm (FIG. 2A) | 200 V/cm (FIG. 2B) | 500 V/cm (FIG. 2C) | 0-400 V/cm (FIG. 3) | 400-100 V/cm (FIG. 4) |
|---|---|---|---|---|---|---|
| 41 | 72 | 267315 | 285570 | 231663 | 2238505 | 233525 |
| 42 | 118 | 314173 | 296041 | 225221 | 1659932 | 207590 |
| 43 | 194 | 295187 | 288121 | 233902 | 1585342 | 215614 |
| 44 | 234 | 266028 | 296556 | 226452 | 1555559 | 207910 |
| 45 | 271 | 234530 | 286551 | 201401 | 1274003 | 189650 |
| 46 | 281 | 244754 | 294239 | 255325 | 1380669 | 197177 |
| 47 | 310 | 143187 | 191084 | 146538 | 1483281 | 204222 |
| 48 | 603 | 147648 | 194253 | 164707 | 1411394 | 145678 |
| 49 | 872 | 110304 | 149061 | — | 1325371 | 101351 |
| 50 | 1078 | 86257 | 100610 | — | 1162954 | 113796 |
| 51 | 1353 | 61032 | 88550 | 147018 | 1131967 | 116819 |

FIG. 6

CAPILLARY ELECTROPHORESIS USING TIME-VARYING FIELD STRENGTH

BACKGROUND OF THE INVENTION

1. Field of The Invention

The present invention relates to electrophoresis, particularly capillary electrophoresis, and more particularly capillary gel electrophoresis.

2. Description of Related Art

Recently, there has been a great deal of activity in DNA analysis by capillary electrophoretic methods ([1] Cohen, A. S.; Najarian, D. R.; Paulus, A; Guttman, A; Smith, J. A.; Karger, B. L.; *Proc. Natl. Acad. Sci. U.S.A.*, 1988, 85, 9660-9663; [2] Paulus, A., Gassmann, E.; Field, M. J.; *Electrophoresis*, 1990, 11, 702-708; [3] Yin, H. F.; Lux, J. A.; Shomburg, G.; *J. High Res. Chrom.*, 1990, 13, 624-627.) Using this new and powerful technology, results have been published on the separation of single-stranded DNA molecules, such as in synthetic DNA analysis ([4] Guttman, A.; Cohen, A. S.; Heiger, D. N.; Karger, B. L.; *Anal. Chem.*, 1990, 62, 2038-2042), as well as in the separation of double-stranded DNA molecules, particularly concerning PCR products and restriction fragments ([5] Schwartz, H. E.; Ulfelder, K.; Sunzeri, F.; Busch, M.; Brownlee, M.G.; *J. Chromatogr.* 1991, 559, 267-283.) It was also demonstrated that high-efficiency, fast separations of DNA molecules can be achieved by the use of linear polyacrylamide gel-filled capillary columns ([6] Heiger, D. N.; Cohen, A. S.; Karger, B. L.; *J. Chromatogr.*, 1990, 516, 33-48; [7] Guttman, A.; Cooke, N.; *J. Chromatogr.*, 1991, 559, 285-294.) Even fragments of the same chain length with different sequences were separated by this method due to differences in molecular conformation ([8] Guttman, A.; Nelson, R. J.; Cooke, N. *J. Chromatogr.*, 1991, 593, 297-303.)

Different field operation techniques have been described recently to achieve better separation of different size DNA molecules, mainly with slab gel electrophoresis. Dennison et al ([9] Dennison, C.; Linder, W. A.; Phillis, N. C. K.; *Anal. Biochem*, 1982, 120, 12-18) employed conical or wedge-shaped slab gels to linearize the logarithmic distribution of bands (nonlinear voltage gradient method) Biggin et al ([10] Biggin, M. D.; Gibson, T. J.; Hong, G. F.; *Proc. Natl. Acad. Sci. U.S.A.*, 1983, 80, 3963-3965) studied the usefulness of high ionic strength anode buffer where the resistance of the gel in the direction of the anode decreases and creates a negative field-strength gradient along the DNA's migration path. They concluded that this particular method is not practical for ultrathin gels, as is also the case for capillary gel electrophoresis ([11] Guttman, A.; Beckman Instruments, Inc., Research and Development, Unpublished results, 1991). Ansorge et al tried using an increasing cross-sectional area of the slab gels producing a field gradient to achieve enhanced sharpening of bands, thereby increasing the number of resolvable bases per gel ([12] Ansorge, W.; Labeit, S.; *J. Biochem. Biophys. Methods*, 1984, 10, 237-243.) Cantor et al ([13] Cantor, C. R.; Smith, C. L.; Mathew, M. K.; *Ann. Rev. Biophys. Biophys. Chem.*, 1988, 17, 287-304) introduced the pulsed field method (changing the direction and magnitude of the field in an oscillating manner), that takes advantage of the elongated and oriented configuration of large DNA (<50 kbp) molecules in gels. Heiger et al [6] described the capillary gel electrophoretic separation of double-stranded DNA molecules up to 23,000 base pairs in size using the pulsed field technique with very low gel concentrations. Although in slab gel operation there are some mechanical difficulties involved in handling low concentration gels ([14] Fangman, W. L.; *Nucl. Acid Res.*, 1978, 5, 653-665), this does not present a problem in capillary electrophoresis techniques. Demana and co-workers ([15] Demana, T.; Lanan, M.; Morris, M. D.; *Anal. Chem.*, 1991, 63, 2795-2797) used an analyte velocity modulation method to increase separation power in capillary gel electrophoresis of DNA restriction fragments.

SUMMARY OF THE INVENTION

The present invention is directed to a technique that provides enhanced separation resolution in electrophoresis. This technique involves the use of a time-varying field strength, which may be progressively increasing or decreasing, constantly or otherwise, as a function of time. The shape of the field strength with respect to time may be continuous or stepwise over time, monotonic or otherwise.

Because the mobility of different size species is a function of the applied electric field, the use of a nonuniform (time varying) electric field increases the resolving power of electrophoresis. This technique has been found to provide enhanced resolution of double-stranded DNA molecules in capillary polyacrylamide gel electrophoresis. It has been found that enhanced separation of DNA restriction fragments of 1 to more than 1000 base pairs in size has been achieved employing the technique of the present invention.

BRIEF DESCRIPTION OF THE DRAWINGS

FIG. 6 is a table showing the theoretical plate number values of the peaks on FIGS. 2-4, calculated by using the System Gold Software Package (Beckman Instruments, Inc., Fullerton, Calif.).

DESCRIPTION OF THE ILLUSTRATED EMBODIMENTS

The following description is of the best presently contemplated mode of carrying out the invention. This description is made for the purpose of illustrating the general principles of the invention and should not be taken in a limiting sense. The scope of the invention is best determined by the appended claims.

The present invention is described below in reference to separation of DNA restriction fragments in capillary electrophoresis, and in particular capillary gel electrophoresis. However, it is understood that the technique of the invention can be to apply to other types of electrophoresis (e.g. slab gel electrophoresis) and for other types of samples (e.g. proteins, peptides).

EXPERIMENTAL SECTION

Figure 1:
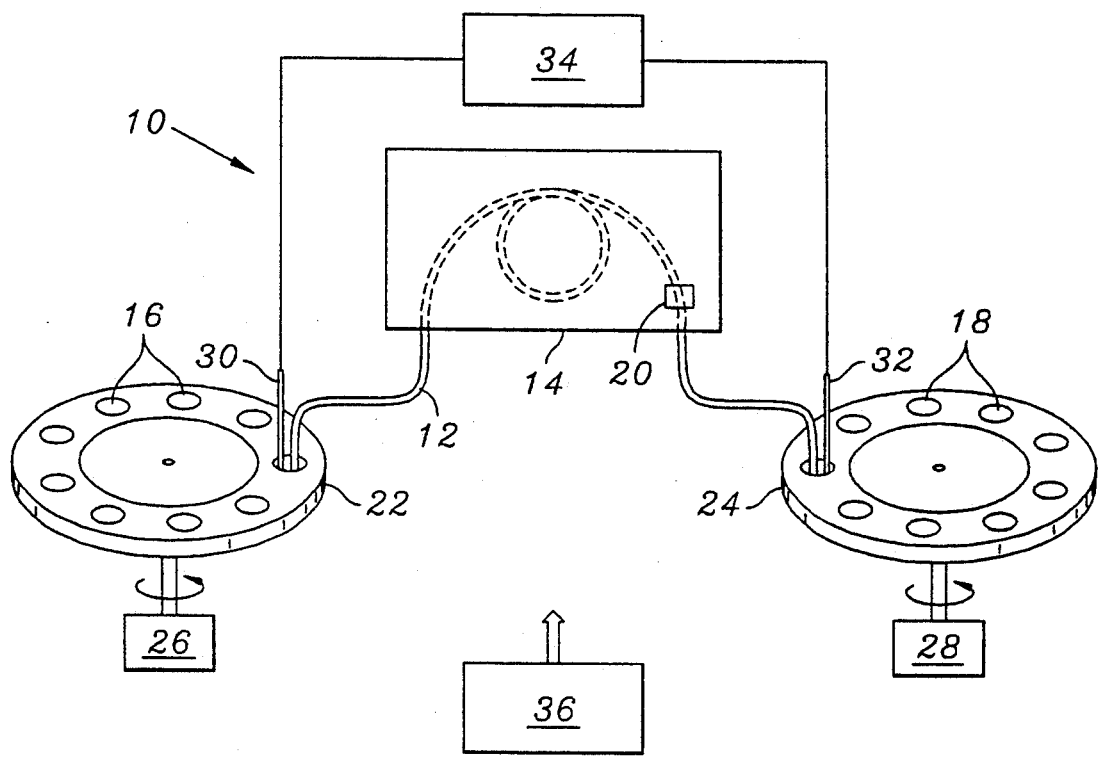
FIG. 1 is a schematic diagram of an automated electrophoresis instrument.

Apparatus. In all of the experiments, the P/ACE TM System 2100 capillary electrophoresis apparatus (Beckman Instruments, Inc., Fullerton, Calif.) was used. Said system 10 is schematically shown in FIG. 1. The details of the system have been omitted since the system is publicly available. In this system, the capillary column 12 is encased in a cartridge 14 which is supported to allow the ends of the capillary to access vials 16 and 18 of electrolyte (liquid or gel) or sample solutions. Capillary referred herein means tubing having inside diameter typically less than 1000 $\mu$m and more typically less than 300 $\mu$m. Coolant is pumped through the cartridge interior for controlling the temperature of the capillary 12. A detector 20 is provided to detect separated species. The vials are carried on carousels 22 and 24 which are rotated by motors 26 and 28 to position selected vials at the ends of the capillary 12. A selected solution can be forced into the capillary by submerging one end of the capillary into the solution and gas pressurizing the vial by conventional means. A low concentration polymerized gel (i.e., polymer network) can be contained in a vial on the carousel and forced into a capillary in the same manner as is done with solution. The gel in the capillary can be replaced by applying a rinse operation mode of the system, whereby the gel in the capillary can be flushed out of the capillary and a fresh gel can subsequently fill the capillary.

The system 10 has a sample injection mode which injects sample from a vial into one end of the capillary by either electromigration or gas pressure injection. Electrodes 26 and 28 are provided to apply the required high voltage (in the order of several hundred volts per cm of capillary) from voltage supply 34 for electromigration injection as well as for carrying out electrophoresis. Electrophoresis is performed with the two ends of the capillary dipped into electrolyte containing vials. The electrolyte can be in the form of buffer solution similar to the buffer used in the process of forming the gel, or in the form of gel (i.e. a gel buffer system). The operation and sequence of various functions of the system are carried out automatically under the control of a controller 36 programmable by the user. These functions include applying a time-varying electric field across the electrodes 26 and 28 in accordance with a user programmed profile such as those described below.

In the experiments set forth below, the cathode is on the injection side and the anode is on the detection side. Therefore, the negatively charged DNA molecules migrate toward the anode in the gel filled capillary column. The separations were monitored on column at 254 nm. The temperature of the capillary column was kept constant at 20° C.,+/−0.1° C., by the liquid cooling system of the P/ACE TM instrument. The electropherograms were acquired and stored on an Everex 386/33 computer. The capillary used is packed with gel as a separation support medium.

Chemicals. The $\phi$X174 DNA Hae-III digest and the pBR322 DNA Msp-I digest restriction fragment mixtures (New England Biolabs, Beverly, Mass.) were diluted with deionized water to a concentration of 25 $\mu$g/ml before injection, and were stored at −20° C. Ultra pure grade acrylamide, Tris, boric acid, EDTA, ammonium persulfate and tetramethylethylenediamine (TEMED) were used in the experiments (Schwarz/Mann Biotech, Cambridge, Mass.). All buffer and acrylamide solutions were filtered through a 0.2 $\mu$m poresize filter (Schleicher and Schuell, Keene, N.H.) and carefully vacuum degassed.

Procedures. Polymerization of the linear polyacrylamide gel was initiated by ammonium persulfate and catalyzed by TEMED in 100 mM Tris-borate, 2 mM EDTA buffer (pH 8.35) prior to inserting the reaction mixture into the 0.1-mm uniform internal diameter fused silica capillary tubing (DB-225, J&W, Inc., Sacramento, Calif.). The polymerization reaction mixture was injected into the capillary by means of a gas-tight syringe (Dynatech, Baton Rouge, La.). The use of low viscosity linear polyacrylamide, not bound to the capillary wall, permits replacement of the gel-buffer system in the capillary column by means of the rinse operation mode of the P/ACE TM instrument. The total length of the gel-filled capillary column was 470 and 670 mm (400 and 600 mm to the detection point), respectively. The samples were injected by the pressure injection mode of the P/ACE TM system, typically 5 sec, 0.5 psi. Estimated injection amount: 0.1 ng DNA.

Time-varying field strength profiles were programmed in the P/ACE TM instrument with continuously increasing or decreasing voltage separation modes. In the stepwise time-varying field separation mode, constant voltages were used for different time periods as specified in the corresponding FIG. 5B.

RESULTS AND DISCUSSION

By the use of a low concentration gel (less than 5% linear polyacrylamide) in capillary electrophoresis, it is possible to achieve good separation of a wide size range of double-stranded DNA molecules. Separations are comparable to or better than those achieved with agarose in slab gel operation [5]. Using a relatively high electric field, DNA molecules can be separated with high resolution in a relatively short time. However, at high field strengths, the electrophoretic mobility of DNA molecules becomes field-dependent ([16] Flint, D. H.; Harrington, R. E.; *Biochemistry*, 1972, 11, 4858–4864). Furthermore, it is known that chain entanglement plays a significant role in the separation of DNA molecules in a gel of a given pore size ([17] Smizek, D. L.; Hoagland, D. A. *Science*, 1990, 248, 1221–1223), this entanglement is a function of the molecular size and the applied electric field [15]. The main challenge is to find the appropriate field for the optimal separation of a mixture of DNA molecules with different chain lengths in a given gel matrix. At low field strengths a sieving effect applies and an inversely proportional relationship between mobility and molecular size is observed ([18] De Gennes, P. G.; *Scaling Concepts in Polymer Physics*, Cornell University Press, Ithaca, N.Y., Ch.3, 1979.) With higher field strengths, a different phenomena appear. The DNA chain becomes more oriented because the field biases the direction of the leading end of the molecule [18]. This leads to an increase in mobility with increasing field strength, particularly for the larger size molecules. In other words, by applying a high electric field, the longer chain length DNA molecules might be partially or completely stretched along the alignment of the field. Thus the electrophoretic mobility of these big molecules become size-independent causing poor separation at high field strengths ([19] Lumpkin, O. J.; Dejardin, P.; Zimm, B. H. *Biopolymers*, 1985, 24, 1573-1593). It should be noted that in capillary polyacrylamide gel electrophoresis this effect appears to occur with fragment lengths longer than 1000 bp. Interestingly, for very short chain length fragments (<300) the separation power might be increased by using high applied electric field [6,19].

Figure 2A:
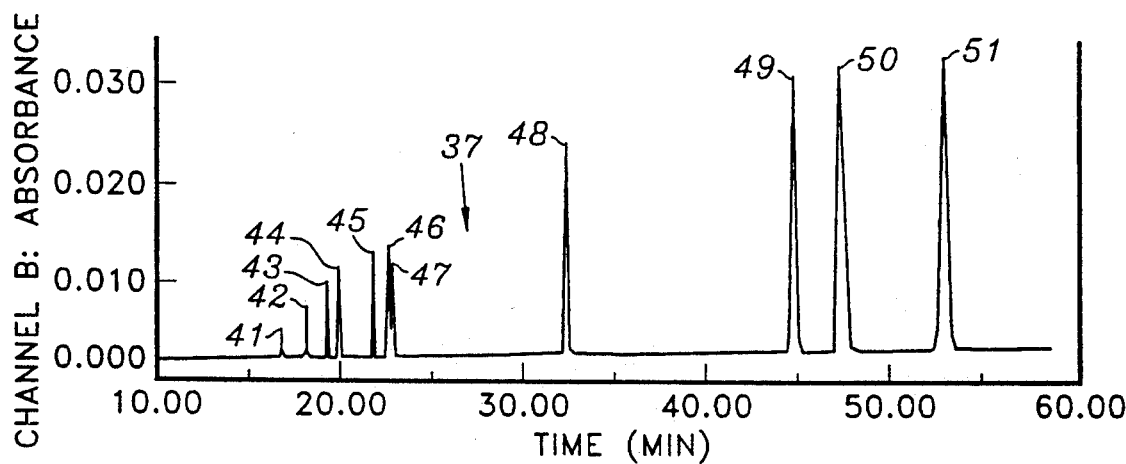
FIG. 2 compares electropherograms showing separation of a $\phi$X174 DNA restriction fragment mixture by capillary gel electrophoresis using different constant applied electric field (isoelectrostatic). (A) 100, (B) 200, (C) 500 V/cm.
Figure 2B:
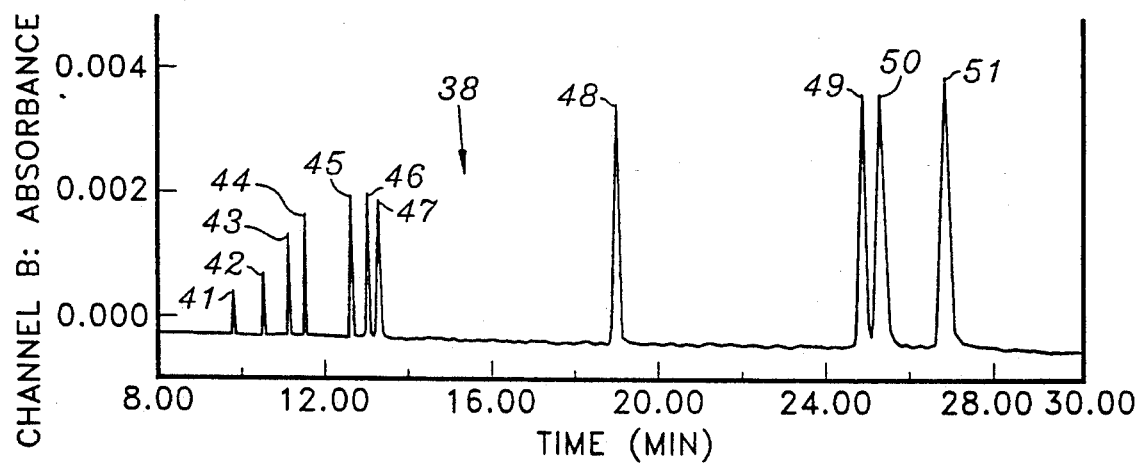
Figure 2C:
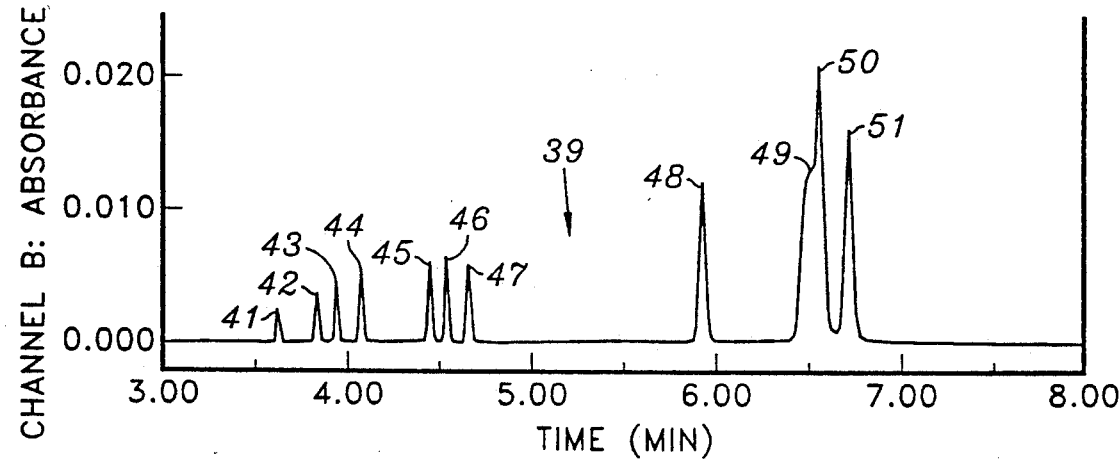

FIG. 2 compares the separations of a φX174 DNA Hae-III restriction fragment mixture using different constant field strengths. Conditions: replaceable polyacrylamide gel column, effective length to detector 40 cm, total length, 47 cm; buffer, 0.1M Tris-borate, 2 mM EDTA (pH 8.35). FIG. 2A shows the electropherogram 37 of the test mixture when 100 V/cm electric field is applied to the gel-filled capillary column. At this low field strength DNA molecules act more like random coils, so good separation can be achieved even for fragments above $10^3$ base pairs (sieving effect [18]). This separation of the larger fragments is attained at the cost of longer separation time (>50 min). However, some of the smaller fragments are not fully resolved. Peaks were identified by their increasing area, which correlates to the chain lengths: 41=72, 42=118, 43=194, 44=234, 45=271, 46=281, 47=310, 48=603, 49=872, 50=1078, 51=1353 base pairs. As FIG. 2A shows, there is an incomplete separation between peak 46 and peak 47 (271- and 281-bp fragments). Similar results have been attributed by Karger and co-workers [6] to diffusional band broadening due to the long separation time in very diluted gel filled capillary columns. By increasing the applied electric field to 200 V/cm, complete separation of all eleven fragments is achieved in 27 min. (see electropherogram 38 in FIG. 2B). The larger DNA molecules probably start to align with the electric field and therefore resolution in the large size range is not as complete as in FIG. 2A. A further increase in field strength to 500 V/cm (see electropherogram 39 in FIG. 2C), causes stronger alignment ([20] Slater, G. W.; Noolandi, J.; *Biopoylmers*, 1986, 25, 431-454) of the larger fragments with a concomitant loss of resolution, since the sieving matrix can no longer separate some of the aligned molecules (peaks 49 and 50). However, the separation time decreases to 7 minutes and the lower molecular weight fragments (peaks 46 and 47) are separated completely due to the high applied electric field [19].

Based on the results shown above it was reasoned that enhanced separation of DNA molecules could be achieved by applying a nonuniform electric field that varies time. In this way all the different molecular weight range DNA molecules can be exposed to the electric field strength that is optimal for their separation.

In capillary polyacrylamide gel electrophoresis of DNA, when a uniform electric field (E) is applied to a charged polyion under steady state conditions [7], the electrophoretic velocity (v) can be expressed by the product of the electric field and the electrophoretic mobility of the DNA molecule at the given field strength ($\mu$):

$$v = \mu E \tag{1a}$$

However, this basic equation should be modified when a nonuniform field is applied [E(t)] since then the applied electric field is changed with respect to time (t) causing a change in the electrophoretic velocity of the polyion. One also should consider that the electrophoretic mobility of the DNA molecule is a function of the electric field [$\mu(E)$], as was reported earlier ([21] Guttman, A.; Cooke, N.; *Anal. Chem.*, 1991, 61, 2038-2042), so one can write:

$$v(t) = \mu(E) E(t) \tag{1b}$$

Equation 1b states that the actual velocity, v(t) of a DNA molecule is influenced by the field strength in use at a given time and by the mobility, which is also a function of the field strength. Thus, when a nonuniform electric field is applied, the electrophoretic acceleration (a) can be expressed as the change in electrophoretic velocity, i.e. the product of the electrophoretic mobility and the field strength at a given time:

$$a = dv/dt = d(\mu E)/dt \tag{2}$$

where dv and dt are the electrophoretic velocity and the time increments, respectively. Based on earlier results [21], as a first approximation one can consider that the mobility of the double stranded DNA molecules has a field independent ($\mu_0$) and a field dependent component:

$$\mu = \mu_0 + S_1 E \tag{3}$$

where $\mu_0$ is an extrapolated value of the electric field vs. the mobility plot to zero field strength for a given chain length DNA molecule and $S_1$ is the slope value of the same plot ($r^2 = 0.987$). Since this slope values show a linear relationship with the chain length of the DNA molecules in the range examined [11], the following equation will hold:

$$S_1 = A + S_2 n \tag{4}$$

where A is a constant for a given gel-buffer system, $S_2$ is the slope of the $S_1$ versus n plot ($r^2 = 0.992$) and n is the chain length (base pair number) of the DNA molecule. Combining equations 1-4 we obtain:

$$a = dv/dt = d[\mu_0 + (A + S_2 n)E]E/dt \tag{5}$$

thus, $$a = \mu_0 dE/dt + (A + S_2 n) dE^2/dt \tag{6}$$
$$\quad\quad\text{I.} \quad\quad\quad\quad \text{II.}$$

where term I is the field strength only and term II is the field and chain length dependent component. As an example, when the electric field strength is a linear function of time:

$$E = B + Ct \tag{7}$$

where B and C are constants, then the electrophoretic acceleration of the polyion can be simply expressed as in equation 6:

$$a = \text{const}_1 + t\, \text{const}_2 \tag{8}$$

Peak efficiency (theoretical plate value N) and resolution ($R_S$) are also affected by the momentary field strength ([22] Karger, B. L.; Cohen, A. S.; Guttman, A. *J. Chromatogr.* 1989, 492, 585–614.) Thus, one can conclude that after the proper substitutions, the change in the theoretical plate number N is a linear function of the acceleration, $$\frac{dN}{dt} = \frac{d}{dt}\left(\frac{aL}{2D}\right) = \frac{d}{dt}\left(\frac{\{\mu_0 + (A + S_{2^n})E\}EL}{2D}\right) \quad (9)$$

where L is the effective length of the capillary and D is the diffusion coefficient of the solute. The change in resolution is proportional to the square root [22] of the acceleration, $dR_S/dt \sim d(a^{\frac{1}{2}})/dt$ when a linearly time-varying field strength is used.

Since different applied electric fields are optimal for the separation of different size DNA fragments [13–16; 19–21], the use of a time-varying field strength gives the opportunity to increase significantly the resolving power of the technique. Time-varying field strength can be used in increasing, decreasing, constant or otherwise, continuous or stepwise modes or in any combination thereof, if necessary. Compared to pulsed field electrophoresis, the fluctuation of the field strength (in case of a profile involving a combination of increasing and decreasing field strength) takes place in periods of at least several minutes (e.g. 1–5 minutes) as opposed to fraction of a second. Pulsed field electrophoresis uses oscillating field of at least several cycles per second (e.g. 50 Hz).

Figure 3:
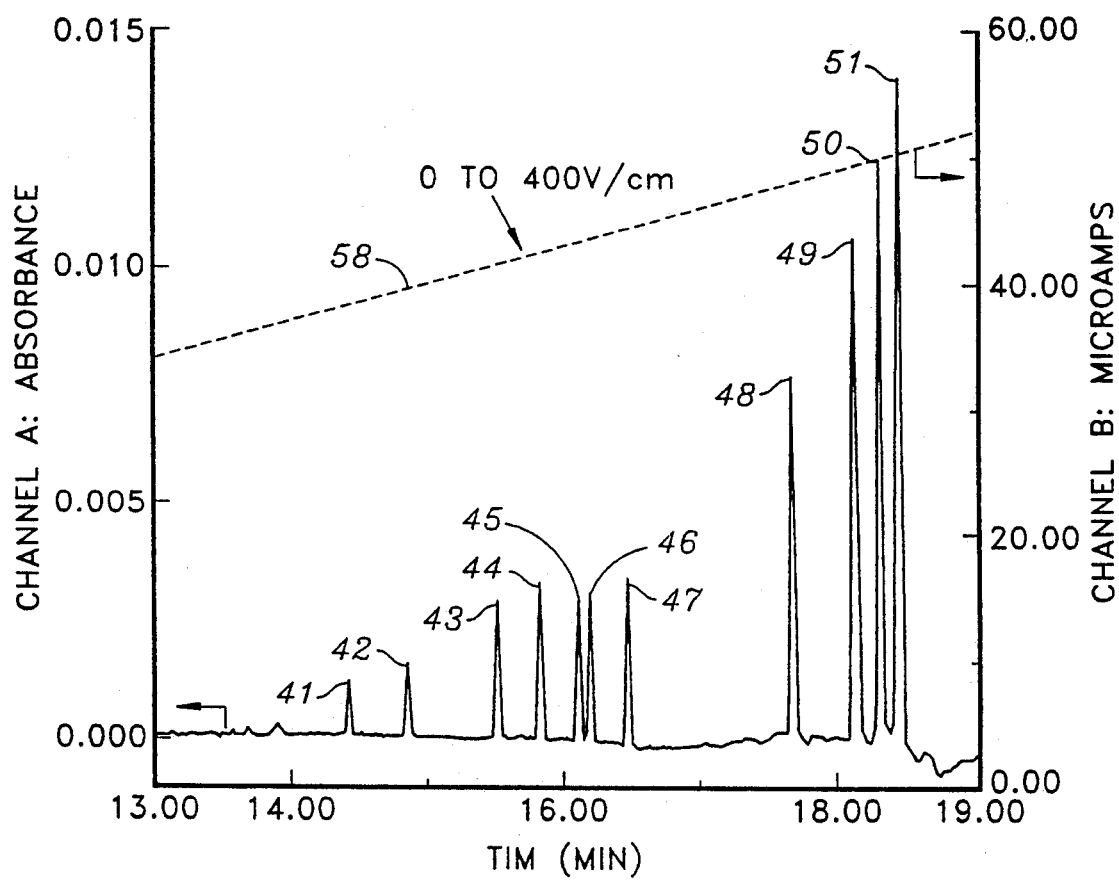
FIG. 3 is an electropherogram showing separation of a $\phi$X174 DNA restriction fragment mixture by capillary polyacrylamide gel electrophoresis using an increasing voltage. Dotted line represents the current output.

FIG. 3 is an electropherogram 56 which shows a separation of the $\phi$X174 DNA restriction fragment mixture using constantly increasing electric field strength over time (0 V/cm to 400 V/cm in 20 min). Other conditions remain the same as before. Because the capillary separation channel has uniform internal diameter, the current varies directly with voltage. It is easier to represent the time-varying voltage by showing the time-varying current in FIG. 3 as a dotted line 58. Full separation of all the test mixture components was achieved in less than 19 min. As FIGS. 3 and 6 show, the apparent efficiency (i.e., theoretical plate number [7]) of the last several peaks (49, 50 and 51) is greater compared to FIG. 2B, where full separation of all the sample components was also attained. In this example, these fragments migrate faster past the detector window due to the higher field strength applied at the last part of the separation. Thus, consistent with the above, the apparent theoretical plate value N, seems to be higher (equation 9, see table FIG. 6). Since $R_S$ changes only by the square root of the field, the resolution was not appreciably enhanced. Separation time was decreased by one-third by using the increasing time-varying field strength method (compare to FIG. 2B).

Figure 4:
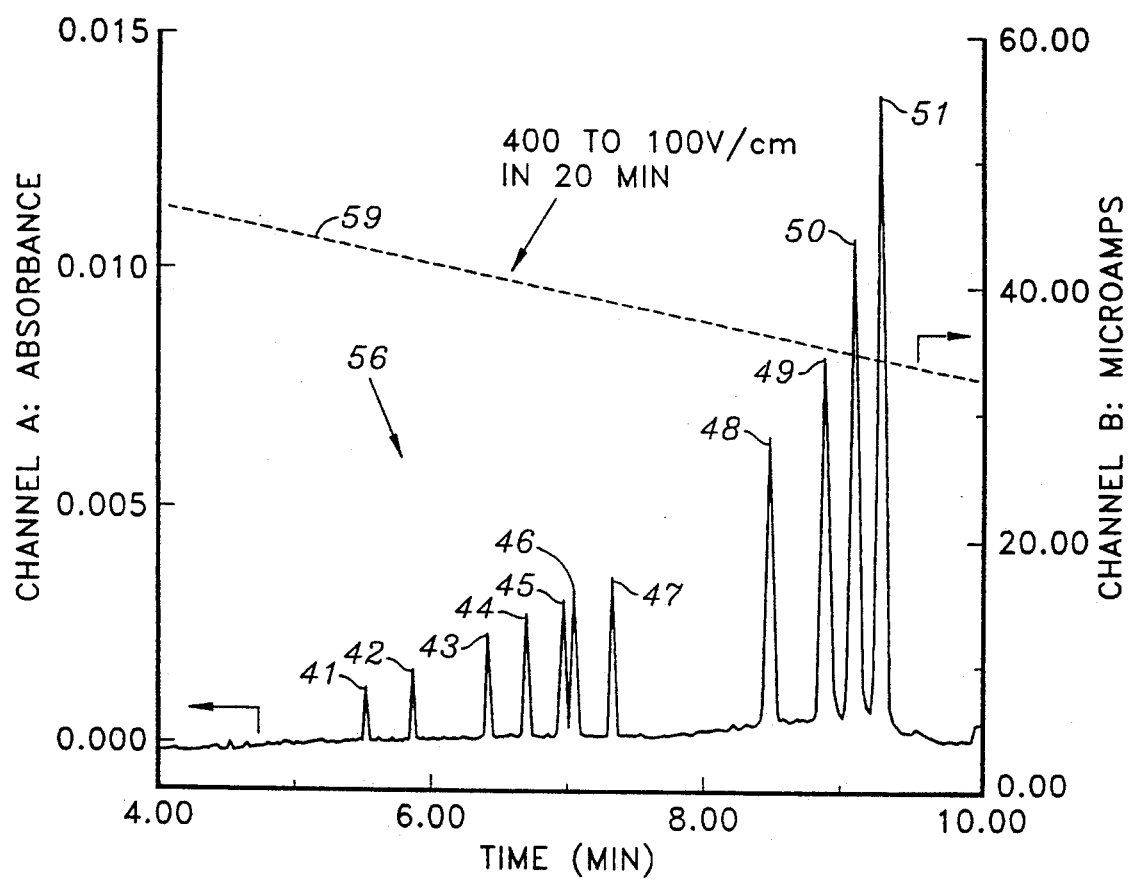
FIG. 4 is an electropherogram showing separation of the a $\phi$X174 DNA restriction fragment mixture by capillary polyacrylamide gel electrophoresis using decreasing voltage gradient. Dotted line represents the current output.

Conversely, the applied electric field can be decreased over time, as shown in FIG. 4. Here, a constantly decreasing field strength gradient of 400 V/cm to 100 V/cm in 20 min (dotted line 59 in FIG. 4) was applied to the linear polyacrylamide network-filled capillary column. Other conditions remain the same. As shown in the electropherogram 56, baseline separation of all eleven components of the $\phi$X174 restriction fragment mixture was achieved in less than 10 min, which is comparable to the separation time shown in FIG. 2C. In the case of FIG. 4, the larger fragments migrated past the detector window slower due to the lower field strength at the end of the separation. This causes an apparent loss in efficiency or theoretical plate number N (equation 9, see table in FIG. 6) and resolution, particularly for the last three peaks.

Figure 5A:
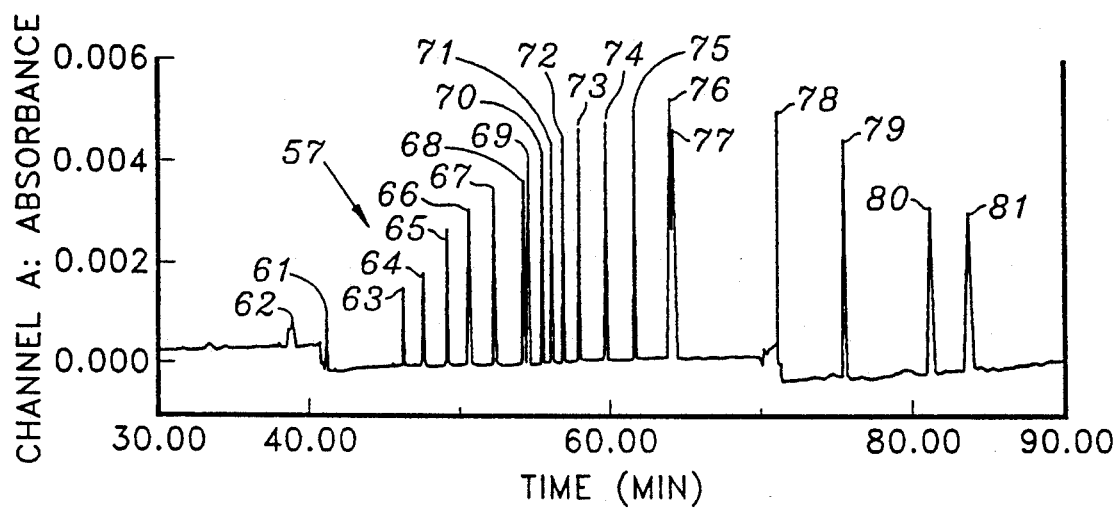
FIG. 5A is an electropherogram showing separation of a pBR322 DNA restriction fragment mixture by capillary polyacrylamide gel electrophoresis using an increasing stepwise gradient field.
Figure 5B:
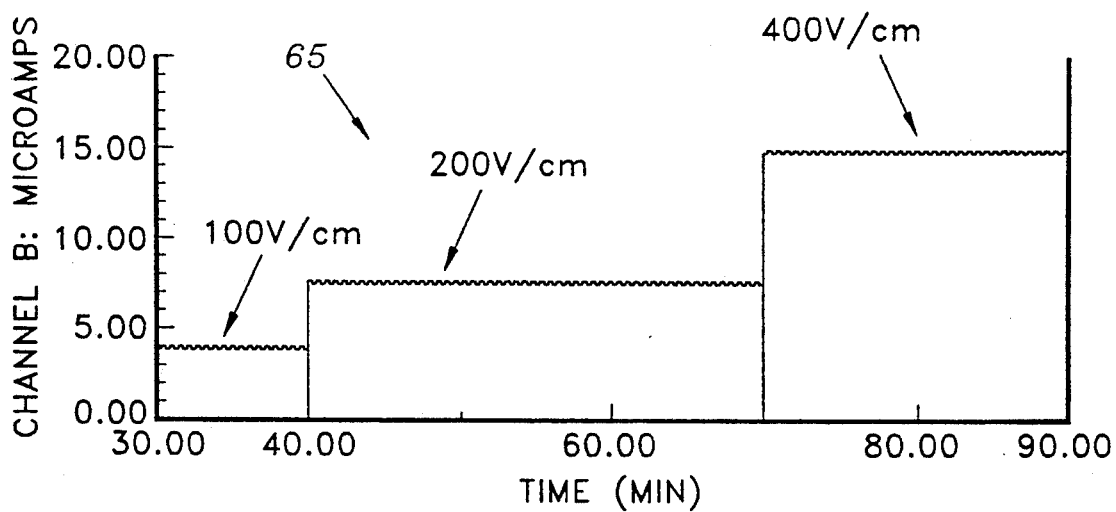
FIG. 5B represents current output.

Time-varying field strength methods can be used in the stepwise mode as well as in the continuous mode. FIG. 5A shows an electropherogram 57 which the separation of a pBR322 DNA restriction fragment mixture employing a stepwise time-varying voltage method in a longer capillary column (effective column length: 60 cm). The method consisted of three consecutive steps, 100 V/cm from 0 to 40 min., 200 V/cm from 40 to 70 min. and 400 V/cm from 70 to 100 min. (see current profile 60 in FIG. 5B). Other conditions remain the same. In this way, full separation of almost all the components was attained. In FIG. 5A, peaks 61–81 corresponds to the chain length: 61=26, 62=34, 63=67, 64=76, 65=90, 66=110, 67=123, 68=147, 69=147, 70=160, 71=160, 72=180, 73=190, 74=201, 75=217, 76=238, 77=242, 78=309, 79=404, 80=527, 81=622 base pairs. It is worth noting the baseline separation of peaks 68 and 69 (147-mers) and peaks 70 and 77 (160-mers), since these components have the same chain lengths but different sequences. These fragments could have been separated previously only by means of capillary affinity gel electrophoresis using ethidium bromide as an intercalating affinity ligand [21].

SUMMARY

A simple time-varying field strength method was introduced in order to increase the resolving power in capillary polyacrylamide gel electrophoresis separation of DNA restriction fragment mixtures. The use of increasing, decreasing, continuous or stepwise voltage techniques showed that the resolving power can be optimized for a given DNA chain length range, and separation time can be significantly reduced. In the study on the separation of the $\phi$X174 DNA restriction fragments by capillary polyacrylamide gel electrophoresis, the best separation with minimum time requirement was achieved by using a continuously decreasing applied electric field. It is important to note that with the use of field strength gradient methods, the apparent peak efficiency and resolution may be misleading since the different size components migrate past the detector window with a velocity that is determined by the voltage in use at that point in time. Other types of time-varying parameters may be employed, such as current, power and temperature and the combination of those can also be used to optimize capillary gel electrophoretic separations of a given sample mixture.

While the invention has been described with respect to the illustrated embodiments in accordance therewith, it will be apparent to those skilled in the art that various modifications and improvements may be made without departing from the scope and spirit of the invention. Accordingly, it is to be understood that the invention is not to be limited by the specific described embodiments, but only by the scope of the appended claims.

I claim:

1. An apparatus for electrophoresis of a mixture of sample components comprising:

a medium suitable for electrophoresis defining a separation path for a mixture of sample components positioned in said path for electrophoresis, wherein the medium is supported in a capillary, and wherein said section of the separation path is uniform in cross-section;

means for applying a time-varying electric field along a section of the separation path in accordance with a user defined electric field profile with respect to time, said field causing electrophoresis of the sample, whereby the electric field profile is selected by the user such that field strength is dependent on the size of the sample components to be separated, wherein said electric field profile is such whereby the electric field increases with time.

2. An apparatus as in claim 1 wherein the medium is a gel.

3. An apparatus as in claim 1 wherein said electric field profile is such whereby the electric field increases with time at a constant rate.

4. An apparatus for electrophoresis of a mixture of sample components comprising:

a medium suitable for electrophoresis defining a separation path for a mixture of sample components positioned in said path for electrophoresis;

means for applying a time-varying electric field along a section of the separation path in accordance with a user defined electric field profile with respect to time, said field causing electrophoresis of the sample, whereby the electric field profile is selected by the user such that field strength is dependent on the size of the sample components to be separated, wherein said electric field profile is such whereby the electric field monotonically increases with time.

5. An apparatus as in claim 4 wherein said electric field profile is such whereby the electric field increases with time at a constant rate.

6. An apparatus as in claim 4 wherein the medium is supported in a capillary, wherein said section of the separation path is uniform in cross-section.

7. An apparatus as in claim 6 wherein the medium is a gel.

8. An apparatus for electrophoresis of a mixture of sample components comprising:

a medium suitable for electrophoresis defining a separation path for a mixture of sample components positioned in said path for electrophoresis, wherein the medium is supported in a capillary, and wherein said section of the separation path is uniform in cross-section;

means for applying a time-varying electric field along a section of the separation path in accordance with a user defined electric field profile with respect to time, said field causing electrophoresis of the sample, whereby the electric field profile is selected by the user such that field strength is dependent on the size of the sample components to be separated, wherein said electric field profile is such whereby the electric field increases step-wise with time.

9. An apparatus as in claim 8 wherein the medium is a gel.

* * * * *